United States Patent [19]
Leonard et al.

[11] Patent Number: 5,811,436
[45] Date of Patent: Sep. 22, 1998

[54] ORAL LIQUID COMPOSITIONS CONTAINING PAROXETINE RESINATE

[75] Inventors: Graham Stanley Leonard, St Albans; David Cooper, Welwyn Garden City, both of United Kingdom

[73] Assignee: SmithKline Beecham plc, Brentford, United Kingdom

[21] Appl. No.: 682,799

[22] PCT Filed: Jan. 30, 1995

[86] PCT No.: PCT/EP95/00319

§ 371 Date: Aug. 1, 1996

§ 102(e) Date: Aug. 1, 1996

[87] PCT Pub. No.: WO95/20964

PCT Pub. Date: Aug. 10, 1995

[30] Foreign Application Priority Data

Feb. 3, 1994 [GB] United Kingdom ............... 9402029

[51] Int. Cl.$^6$ ....................................... A61K 9/18
[52] U.S. Cl. ............................. 514/321; 424/267
[58] Field of Search .................... 514/321; 424/237

[56] References Cited

U.S. PATENT DOCUMENTS 4,007,196  2/1977  Christensen et al. ............... 424/267
5,476,654  12/1995  Conte et al. ........................ 514/360

FOREIGN PATENT DOCUMENTS

WO A 91/13612  9/1991  WIPO.

*Primary Examiner*—Keith MacMillan
*Attorney, Agent, or Firm*—Edward T. Lentz

[57] ABSTRACT

An oral liquid pharmaceutical composition comprising a paroxetine-Amberlite IRP88 complex.

9 Claims, No Drawings

ORAL LIQUID COMPOSITIONS CONTAINING PAROXETINE RESINATE

This application is a 371 of PCT/EP95/00319, filed Jan. 30, 1995, which claims priority to GB 9402029.4 filed Feb. 3, 1994.

The present invention relates to novel formulations and to the use of such a formulation in the treatment and/or prevention of certain disorders.

U.S. Pat. No. 4,007,196 describes certain compounds which possess anti-depressant activity. One specific compound mentioned in this patent is known as paroxetine and which has the following formula:

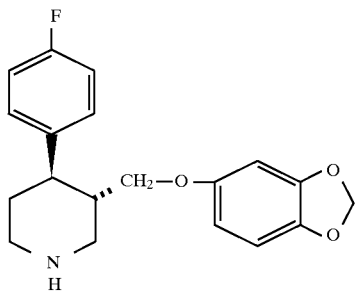

This compound has been approved for human use and is being sold in many countries around the world as an anti-depressant agent All paroxetine sold to date has been in the form of oral swallow tablets.

Many physicians have expressed a desire to be able to prescribe an oral liquid containing paroxetine and some have even made their own oral liquid by crushing conventional swallow tablets and mixing them with water. There are however, a number of draw-backs to this oral liquid, firstly paroxetine has a very bitter taste which is highly noticeable when administered as an oral liquid, secondly such oral liquids have poor stability qualities and have a shelf-life of only a few days.

WO 91/13612 relates to the sustained release of pharmaceuticals using compositions in which the drug is completed with an ion-exchange resin. The specific ion-exchange resin described in this published patent application is AMBERLITE IRP 69, a sodium polystyrene sulphonate resin.

When AMBERLITE IRP-69 is used to complex with paroxetine it was found that whilst the taste was effectively masked the composition had an unacceptably low bioavailability when compared to a swallow tablet.

It has now been found that AMBERLITE IRP 88, an acrilin potassium resin can be used to form a stable taste masted complex with paroxetine and which complex has acceptable bioavailability when compared to the conventional swallow tablet.

Accordingly, the present invention provides an oral liquid pharmaceutical composition comprising a paroxetine-AMBERLITE IRP-88 complex.

AMBERLITE IRP-88 is commercially available from Rohm & Haas in a pharmaceutically acceptable grade.

The oral liquid pharmaceutical composition is prepared in conventional manner such as by mixing paroxetine and AMBERLITE IRP-88 together in an aqueous medium. Suitably the IRP-88 and paroxetine are present in a ratio of 1:1 to 2:1. It should be appreciated that superior taste masking properties are obtained with a 2:1 ratio.

Other pharmaceutically acceptable excipients may also be added such as thickeners such as Keltrol and/or Avicel (in particular Avicel CL 611); dispersants such as propylene glycol; moisture retaining agents such as glycerol; sweetners such as sorbitol and sodium saccharin buffering agents such as citric acid and sodium citrate; preservatives such as sodium benzoate and mixtures of methyl and and propyl parabens (parahydroxybenzoates), artificial colours such as F D and C Yellow No. 6 Sunset Yellow; flavouring such as Givaudan Natural Orange and/or Lemon; and antifoaming agents such as silicone anti-foam.

Preferably the amounts of buffering agents are controlled to give a pH of 4 to 6. Most preferably a pH of 4.5 to 6.0.

The amount of paroxetine used is adjusted such that in a single unit dose there is a therapeutically effective amount of paroxetine. Preferably the unit dose contains from 10 to 100 mg paroxetine (as measured in terms of the free base). More preferable the amount of paroxetine in a unit dose is 10 mg, 20 mg, 30 mg, 40 mg or 50 mg. The most preferred amount of paroxetine in a unit dose is 20 mg of paroxetine.

Preferably the volume of liquid in a unit dose is in the range 5 to 20 ml most preferably 10 ml.

Preferably paroxetine used in the formulation is in the form of the hydrocholide hemi-hydrate which may be prepared according to the procedures outlined in U.S. Pat. No. 4,721,723.

Suitable procedures for preparing paroxetine include those mentioned in U.S. Pat. Nos. 4,009,196, 4,902,801, 4,861,893 and 5,039,803 and PCT/GB 93/00721.

It has been mentioned that paroxetine has particular utility in the treatment of depression, paroxetine may also be used in the treatment of mixed anxiety and depression, obsessive compulsive disorders, panic, pain, obesity, senile dementia, migraine, bulimia, anorexia, social phobia and the depression arising from pre-menstrual tension and adolescence.

The present invention therefore also provides a method of treating or preventing any of the above disorders which comprises administering an effective or prophylatic amount of an oral liquid pharmaceutical composition comprising a paroxetine-AMBERLITE IRP-88 complex to a sufferer in need thereof.

The present invention further provides the use of an oral liquid pharmaceutical composition comprising a paroxetine-AMBERLITE IRP-88 complex in the manufacture of a medicament for treating or preventing the above disorders.

The present invention yet further provides a pharmaceutical composition for use in the treatment or prevention of the above disorders which comprises a paroxetine-AMBERLITE IRP-88 complex admixed with a pharmaceutically acceptable carrier.

The following examples illustrate the present invention:

EXAMPLE 1

(1:1) Ratio of AMBERLITE IRP-88 to paroxetine

|  | mg/10 ml |
|---|---|
| Paroxetine hydrochloride † | 22.8 |
| AMBERLITE IRP 88 (<63 µm) | 22.8 |
| Keltrol | 40.0 |
| Propylene Glycol | 350.0 |
| Glycerol | 350.0 |
| Sorbitol (70%) | 4000.0 |
| Citric acid | 15.0 |
| Sodium Citrate | 10.0 |
| Sodium benzoate | 10.0 |
| Sodium Saccharin | 5.0 |

| | mg/10 ml |
|---|---|
| Sunset Yellow | 0.5 |
| Givaudan Natural Orange | 1.0 |
| Givaudan Natural Lemon | 2.0 |
| Antifoam Silicone | 20.0 |
| Water to | 10.0 |

EXAMPLE 2

(2:1) Ratio of AMBERLITE IRP to paroxetine

| | mg/10 ml |
|---|---|
| Paroxetine hydrochloride (<180 microns) | 22.8 |
| AMBERLITE IRP 88 (<200 mesh) | 40.0* |
| Avicel CL 611 | 300.0 |
| Propylene Glycol | 500.0 |
| Glycerol | 500.0 |
| Sorbitol (70%) | 4000.0 |
| Citric acid (anhydrous) | 15.0 |
| Sodium Citrate (dihydrate) | 10.0 |
| Methyl parahydroxybenzoate | 20.0 |
| Propyl parahydroxybenzoate | 6.0 |
| Sodium Saccharin | 5.0 |
| FD&C Yellow No. 6 | 0.9 |
| Givaudan Natural Orange 74388-74 | 1.0 mcl |
| Givaudan Natural Lemon 74940-74 | 2.0 mcl |
| Silicone Antifoam 1510 | 20.0 |
| Water to | 10.0 |

*on an Anhydrous basis

EXAMPLE 3

As above but 40.0 mg was replaced with 300 mg of Avicel CL 611.

EXAMPLE 4

As above but 15 mg of Keltrol and 300 mg of Avicel CL 611 was used.

We claim:

1. An oral liquid pharmaceutical composition comprising a paroxetine-AMBERLITE IRP-88 complex.

2. A process for preparing a pharmaceutical composition as defined in claim 1 which process comprises mixing paroxetine and AMBERLITE IRP-88 together in aqueous medium.

3. A process according to claim 2 in which the molar ratio of AMBERLITE IRP 88 to paroxetine is 1:1 to 2:1.

4. A pharmaceutical composition according to claim 1 in which any one or more of the following is added; thickeners, dispersants, moisture retaining agents, sweeteners, buffering agents, preservatives, artificial colours, flavourings and anti-foaming agents.

5. A pharmaceutical composition according to claim 4 in which the amount of buffering agents are controlled to give a pH of 4 to 6.

6. A pharmaceutical composition according to claim 4 which is in the form of a unit dose.

7. A pharmaceutical composition according to claim 6 in which the amount of paroxetine in the unit dose is 10 mg, 20 mg, 30 mg, 40 mg, or 50 mg.

8. A pharmaceutical composition according to claim 1 in which the paroxetine is in the form of the hydrochloride hemihydrate.

9. A method of treating or preventing mixed anxiety and depression, obsessive compulsive disorders, panic, pain, obesity, senile dementia, migraine, bulimia, anorexia, social phobia and depression arising from pre-menstrual tension and adolescence which comprises administering an effective or prophylatic amount of an oral liquid pharmaceutical composition as defined in claim 1, according to any one of claims 1 and 4 to 8 to a sufferer in need thereof.

* * * * *